US008309024B2

(12) United States Patent
Redko et al.

(10) Patent No.: US 8,309,024 B2
(45) Date of Patent: Nov. 13, 2012

(54) METHODS AND SYSTEMS FOR NON-DESTRUCTIVE DETERMINATION OF FLUORINATION OF CARBON POWDERS

(75) Inventors: Volodymyr I Redko, Coral Springs, FL (US); Elena M Shembel, Coral Springs, FL (US); Volodymyr S Khandetskyy, Dnipropetrovsk (UA); Dayal T Meshri, Tulsa, OK (US); Isaac A Angres, Gaitherburg, MD (US); Robert Adams, Owasso, OK (US); Dmytro Sivtsov, Dnipropetrovs (UA); Oxana V Redko, Dnipropetrovsk (UA); Tymofiy V Pastushkin, Ft. Lauderdale, FL (US)

(73) Assignee: Enerize Corporation, Coral Springs, FL (US)

( * ) Notice: Subject to any disclaimer, the term of this patent is extended or adjusted under 35 U.S.C. 154(b) by 490 days.

(21) Appl. No.: 12/386,823

(22) Filed: Apr. 23, 2009

(65) Prior Publication Data

US 2009/0267623 A1    Oct. 29, 2009

Related U.S. Application Data

(60) Provisional application No. 61/125,196, filed on Apr. 23, 2008.

(51) Int. Cl.
*G01N 15/06*    (2006.01)
*G01N 33/00*    (2006.01)
*G01N 33/48*    (2006.01)

(52) U.S. Cl. ......... 422/50; 422/401; 422/402; 422/68.1; 422/82.01; 422/82.02; 422/83

(58) Field of Classification Search .................... 422/50, 422/401, 402, 68.1, 82.01, 82.02, 83
See application file for complete search history.

(56) References Cited

U.S. PATENT DOCUMENTS

| 4,208,624 A | 6/1980 | Miller |
| 4,303,885 A | 12/1981 | Davis et al. |
| 4,535,239 A | 8/1985 | Brighton |
| 5,541,510 A | 7/1996 | Danielson |
| 5,552,704 A | 9/1996 | Mallory et al. |
| 5,859,537 A | 1/1999 | Davis et al. |
| 5,889,401 A | 3/1999 | Jourdain et al. |

(Continued)

FOREIGN PATENT DOCUMENTS

JP    04058143 A    2/1992

(Continued)

OTHER PUBLICATIONS

Matiss I. Capacitance probes for nondestructive testing. Riga, Publishing House "Zinatne", 1982.

(Continued)

*Primary Examiner* — Brian J Sines
(74) *Attorney, Agent, or Firm* — Morgan Lewis & Bockius LLP; Richard F. Trecartin

(57) ABSTRACT

A system for non-destructive determination of the degree of fluorination in carbon monofluoride (CFx) during the process of CFx synthesis is described. The system includes a measuring generator containing a capacitive sensor for measuring a respective capacitance, a base generator containing a capacitive sensor for measuring a base capacitance, and a processor for determining a difference between the respective capacitance and the base capacitance. The system is configured to determine the degree of fluorination based on the difference between the respective capacitance and the base capacitance.

10 Claims, 16 Drawing Sheets

U.S. PATENT DOCUMENTS

| | | | |
|---|---|---|---|
| 6,076,396 | A | 6/2000 | Dadachanji et al. |
| 6,288,536 | B1 | 9/2001 | Mandi et al. |
| 6,479,990 | B2 | 11/2002 | Mednikov et al. |
| 6,489,776 | B1 * | 12/2002 | Stowe et al. ............... 324/458 |
| 6,507,200 | B2 | 1/2003 | Brandelik et al. |
| 6,593,738 | B2 | 7/2003 | Kesil et al. |
| 6,707,297 | B2 | 3/2004 | Nath et al. |
| 6,756,791 | B1 | 6/2004 | Bhushan et al. |
| 6,762,604 | B2 | 7/2004 | Le |
| 6,856,140 | B2 * | 2/2005 | Talanov et al. ............. 324/638 |
| 6,894,616 | B1 | 5/2005 | Foster |
| 2005/0116724 | A1 * | 6/2005 | Red'ko et al. ............... 324/649 |
| 2006/0109003 | A1 * | 5/2006 | Redko et al. ................ 324/240 |
| 2009/0267621 | A1 | 10/2009 | Redko et al. |

FOREIGN PATENT DOCUMENTS

JP  06294764 A  10/1994

OTHER PUBLICATIONS

Sobolev V.S., Shkarlet Yu.M., Strap and screen type probes, Novosibirsk, Nauka Publishers, 1967.

Larry K Baxter, Capacitive Sensors (Design and Applications), IEEE Press, New York, 1997.

J W Orton and M J Powell, The Hall effect in polycrystalline and powdered semiconductors. Reports on Progress in Physics, vol. 43, 1263 (1980).

R. Kubacki, L. Nowosielski & R. Przesmycki. A measurement technique for the electric and magnetic properties of powdered ferrites. Computational Methods and Experimental Measurements XIV, Transactions Wessex Institute, 2009.

G. Bogdanov et al., A new apparatus for non-destructive evaluation of green-state powder metal compacts using the electrical-resistively method. Meas. Sci. Technol. 11: 157-166 (2000).

Aida Espinola, Pablo Mourente Miguel et al. Electrical properties of carbons—resistance of powder materials. Carbon. 24(3): 337-341 (1986).

S. O. Nelson, Density-permittivity relationships for powdered and granular materials. IEEE Transactions on Instrumentation and Measurement, 54(5): 2033-2040 (2005).

V. Red'ko, E. Shembel, et al. Non-contact electromagnetic control methods of the specific conductivity powders materials, solid inorganic and polymer film. 3rd MENDT—Middle East Nondestructive Testing Conference & Exhibition—Nov. 27-30, 2005 Bahrain, Manama.

Reinhold Ludwig, Georg Leuenberger et al. Electric Voltage Predictions and Correlation with Density Measurements in Green-State Powder Metallurgy Compacts. Journal of Nondestructive Evaluation, 21(1): 1-8 (2002).

* cited by examiner

METHODS AND SYSTEMS FOR NON-DESTRUCTIVE DETERMINATION OF FLUORINATION OF CARBON POWDERS

CROSS-REFERENCE TO RELATED APPLICATIONS

This application incorporates by reference in its entirety and claims priority to Provisional Application No. 61/125,196, Filed Apr. 23, 2008.

FIELD OF THE INVENTION

The present invention relates to non-destructive testing for determination of physical-chemical properties of powdered materials in particular especially as related to the quality control of powdered materials used in battery manufacturing industry.

BACKGROUND OF THE INVENTION

In 1970-1971 in the US and Japan there were patents issued according to which graphite monofluoride, which has been known since 1934, as well as some fluorinated products of carbonaceous compounds were most energy effective and safe cathode material, in comparison with any other known inorganic cathode materials for lithium batteries.

Along with application CFx for Li-ion battery the CFx material also supplied for non-battery applications with lubrication additives being the major growth area. Other applications include additives in dry inks, additives in elastomeric seals, oxidation resistant catalyst supports and chromatographic column packing.

The main purpose of fluorination of graphite and most of other carbonaceous compounds under high temperatures (200-600° C.) is attaining, as a rule, maximum level of fluorination of the initial carbonaceous compounds. This results in obtaining 44-61% of fluorine content in the fluorinated products. Such fluorine content corresponds the compounds in the range of $C_2F$-$CF_{1.0}$. Under certain conditions, superstoichiometric fluorocarbons materials $CF_{1+x}$. (x=0.12-0.33) can be obtained.

Determining the structure of CFx compounds are very complex problem. This is explained by the fact that monocrystalline samples of $CF_x$ cannot practically be obtained. Similarly, it is difficult to have calibrated data on x-ray structural $CF_x$ analysis. As a result, the diagnosing of the physical and chemical properties the inorganic fluorocarbons and detecting the interaction between their chemical composition, structure and properties seems rather difficult.

Lithium/carbon monofluoride (Li-CFx) batteries with a solid-cathode based on CFx can provide optimized reliability, safety, cost and performance of the batteries. This type of batteries have achieved broad acceptance in a number of expanding high performance military, consumer and industrial applications Features of Li/CFx batteries includes:
outstanding shelf life and excellent performance over a wide temperature range;
stable discharge voltage;
high energy density and discharge voltage
enhanced safety by the use of carbon-monofluoride electrode material and a non-corrosive, non-toxic electrolyte;
excellent leak resistance;
shelf life of ten years or more Operating properties of Li/CFx battery in great degree depended on active materials—CFx properties. Some of the main important properties is the degree of fluorination which influences effects CFx conductivity, operating range of the voltage during discharge and efficiency of CFx based cathode. Therefore it is very important to evaluate the level of CFx degree of fluorination during synthesis process.

Cathode materials based on the carbon fluoride, often referred to as carbon fluoride, polycarbon monofluoride, CFx or graphite fluoride is a solid, structural, non-stoichiometric fluorocarbon of empirical formula (CFx) n where 0<x<1.25.

Graphitized petroleum coke is a main source of raw carbon and the reaction is greatly dependent on the graphitization temperature and degree of graphitization. The natural graphite, heat-treated blacks, carbon fibers and cloths are also used as an initial material. The reaction temperature depends upon type of raw material, reactor design, end use application and desired degree of fluorination.

During the process of the initial materials fluorination the level of "x" increases. Properties CFx in great degree depended from level of "x" in structure. Level of "x" influences of materials structure and properties and as results influences of delay of voltage on the beginning of the discharge process and operating range of voltage during discharge.

The common test of the level of the carbon fluorination includes several methods: XRD,XPS (X-ray photospectroscopy), XES (X-ray emission spectra) and FTIR analysis. These methods are labour-intensive and cannot provide the in-site test of the product during manufacture process. These methods demand special conditions for protection of staff.

SUMMARY OF THE INVENTION

Development an electromagnetic-based non-destructive method to determine the degree of fluorination during the synthesis of CFx is the main objectives of this invention. The method is based on determining the physical properties CFx. This method has the following features:
Assurance that the requested properties and quality of the product are maintained
Reduced time of synthesis and analysis
Avoiding loss of materials and energy The invention includes the method of determination properties of CFx, the electronic units with the transducers, as well as electronic units for processing the informative signal to be acquired and analyzed by operator, and finally, for control the electro-mechanical scanner for measurements across pallet area.

The major advantages over existing ones the physical non-destructive method and devices developed in the presented invention for evaluation the level of CFx degree of fluorination are the following:
Reliability due to its non-destructive nature;
Efficient, fast, simple and in expensive to implement;
Easy to automate;
Safe and less expensive than X-Ray Method. Our method does not require any special protections for operators
Precise determination of materials composition;
Provides 100% control of the quality of the end product.

Non-destructive electromagnetic method developed in this invention for evaluation the electrical and electromagnetic properties the fluorocarbon that is synthesized is the promising method of the evaluation level of $CF_x$ degree of fluorination during the continuous process of fluorination.

The electronic conductivity is one of the important CFx properties which influences on operational properties of the Li-CFx cell. Electronic conductivity CFx depends on structure initial material (petro-coke, carbon black, graphite, carbon fiber), distribution of the particle size and conditions of the fluorination.

Moreover because electronic conductivity depends on degree of fluorination and materials structure the information about electronic conductivity is very important and for other CFx application.

In particular, the specific electric conductivity of material decreases when the degree of the high temperature fluorination of graphite powder or of carbonaceous materials increases. In defining content of fluorine in the CFx this material turns practically into dielectric. Measurement the specific conductivity of superstoichiometric powder of fluorinated graphite using the eddy current electromagnetic field, in accordance with the invention showed that even at 10% of fluorine content in the powder the material turns into dielectric.

Therefore in order to determine the degree of graphite fluorination or the percentage of fluorine in the powder of fluorinated graphite and of other fluorocarbon materials we used the dielectric permeability as an informative parameter. It was computed by equation (3) taking into account the form of transducer, which is presented in the invention which is described herein.

In terms of industrial production the process of high temperature fluorination is conducted in metal-made containers wherein the initial material is placed. Therefore appropriate to determine the degree of powder fluorination in such containers in the process of fluorination or after the process has been ended. This procedure allows to learn how the CFx composition changes in the whole container area, id est to determine the magnitude of fluorine in the powder in different parts of the container. These data are very important for attaining optimal parameters of fluorination process. The parameters should ensure uniform level fluorination of the powder throughout the container the process of high temperature fluorination is conducted in metal-made containers wherein the initial material is placed. Therefore it is appropriate to determine the degree of powder fluorination in such containers in the process of fluorination or after the process has been ended. This procedure allows to learn how the CFx composition changes in the whole container area, id est to determine the magnitude of fluorine in the powder in different parts of the container. These data are very important for attaining optimal parameters of fluorination process. The parameters should ensure a uniform level of fluorination of powder throughout the container.

To execute calibrating of transducer, which is used to determine electromagnetic properties of powder $CF_x$, samples of various compounds $CF_x$ have to be prepared in advance in laboratory environment. Standard compound samples and minimum 7 samples of compounds, which deviate from standards, are to be prepared. Number of samples for each deviation should be minimum 5. The samples are used in constructing calibration charts. On the basis of the calibration charts, electromagnetic parameters measured, which describe CFx, are analysed by an instrument, according to a special program, and then a conclusion is made on the percentage of carbon fluorination.

Results of evaluation of CFx level of fluorination degree using non destructive rapid method and device have a high level of correlation with the results of the chemical analysis. The level of the correlation is 0.976. The calibration curve has a linear character (nature) with a high level of correlation.

The results of the non-destructive evaluation the level of the uniform distribution of the CFx degree of fluorination on the pallet can be used for optimization the parameters of the fluorination. Results of the rapid non-destructive analysis of the CFx compositions show that multiple measurements across the surface of a pallet, after measurement results were averaged out, will yield more accurate results than a single chemical analysis of a sample.

DETAILED DESCRIPTION OF THE INVENTION

Figure 1:
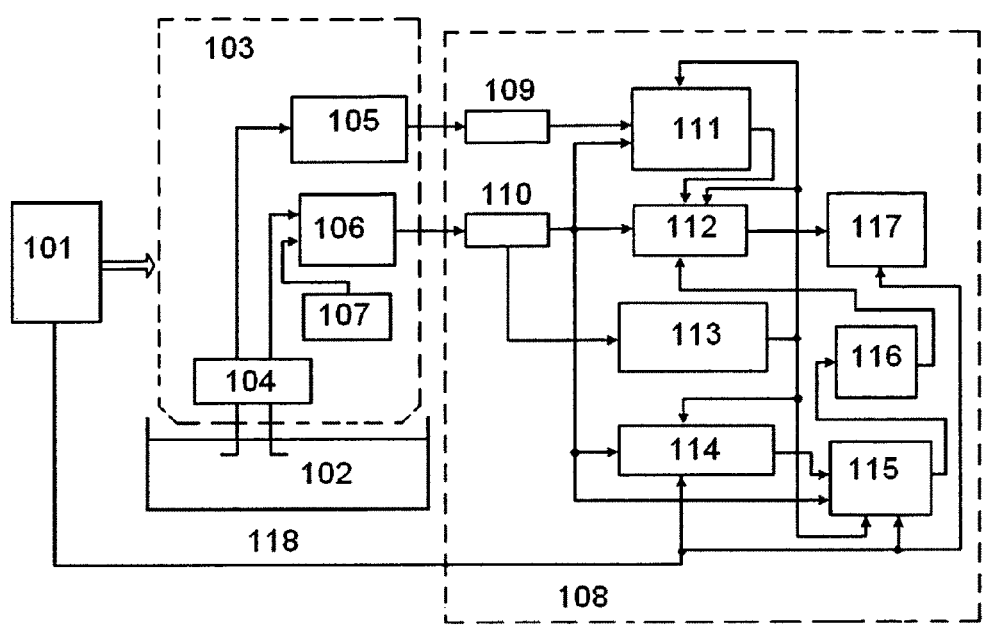
FIG. 1 illustrates operational diagram of the device where: 101 is the scanner; 102 is the pallet filled with fluorinated graphite powder; 103 is the remote measuring transducer; 104 is the measuring generator; 105 is the block for measuring Q-factor; 106 is the frequency subtraction block; 107 is the base generator; 108 is the special computing device; 109 is the analog-digital transducer; 110 is the analog-digital transducer; 111 is the block for comparative analysis; 112 is the calibration block; 113 is the block for determining the beginning of inserting; 114 is the extrapolation block; 115 is the block for measuring difference; 116 is the block for comparison with threshold; 117 is the registration block; 118 is the transmission line signaling the end of inserting in 114, 115, 117.

To obtain fluorocarbon, initial carbonaceous powder is placed in a flat pallet. The pallet is placed into a reactor which is a special furnace to fluoride the material. To evaluate material quality after it has been fluorinated, powder CFx is processed throughout all pallet surface using the method and device that are developed in invention presented here. This procedure ensures 100% control of the material processed.

Method and device developed in presented invention allow the individual portions of fluorocarbon powder can also be evaluated separately. To evaluate in this way, a certain portion of powder is placed in a pallet made for that particular power quantity.

In accordance with the invention, the method of measuring quantity of fluorine in fluorocarbon, which is contained in an aluminum pallet, is based on the dependence of fluorine content in fluorocarbon and dielectric permeability of the powder. Evaluation of powder CFx can be made directly in the pallet, wherein fluoridating is conducted. Information parameter in this event is the magnitude of powder CFx dielectric permeability. The higher the level of degree of fluorination of CFx (fluorine content in the powder CFx) the bigger change in magnitude of dielectric permeability.

Prior to testing powders of fluorocarbon CFx, which is synthesized in a reactor, testing of a set of samples, prepared particularly for this purpose, is conducted. The test is conducted with chemical analysis. These results are used for preparing the calibration graph.

The sensor for evaluation the physical chemical properties of CFx (FIG. 2) is made in the form of metal rings connected in a certain way. The sensor has its own complex capacitance, which changes when sensor is placed in powder. The greater degree of saturation of powder with fluorine, (level of CFx degree of fluorination) the greater the change in value dielectric permeability (permeability).

Prior to testing CFX, transducer self-capacitance and resonance circuit Q-factor are measured. Transducer is an element of resonance circuit. These initial system parameters are determined in the system without fluorocarbon powder.

Magnitude of resonance circuit self-capacitance Q-factor is described by the equation (1):

$$Q_0 = \frac{L}{C_0 r_L}, \tag{1}$$

Where:
L is circuit inductance,
$C_0$ is a self-capacitance,
$r_L$ is resistance of active losses of inductance coil.

When $C_0$ and $Q_0$ have been measured, transducer is placed on the surface of powder tested. Then transducer is lowered into the powder to the depth, which is controlled by a special lowering-hoistering mechanism. In the process of insering time dependencies of resonance circuit Q-factor and transducer capacitance are measured and stored.

Q-factor of transducer inserted in powdered material is computed by the equation (2)

$$Q_1 = \frac{L}{(C_0 + C_d)(r_L + r_d)}, \tag{2}$$

Where $C_d$ is an added transducer capacitance

The value of added capacitance $C_d$ changes in proportion to effect of powder CFx dielectric permeability on the field of the transducer. When fluorine content increases in powder added capacitance $C_d$ decreases slowly; it may be computed for coplanary transducer following the equation (3)

$$C_d = \frac{\varepsilon_0 \varepsilon_r L}{\pi} \ln \frac{(s+b)^2}{s(s+2b)}, \tag{3}$$

where
$C_d$ is a capacitance, F,
$\varepsilon_0$=8.8541878×10$^{-12}$ F/m,
$r_d$ is a resistance of dielectric losses in powder
$r_L$ is a resistance of dielectric losses in inductance coil
$\varepsilon_r$ is a relative dielectric constant (1 for vacuum) relative dielectric permeability
π=3.14,
L, b are the length and width of one plate of coplanary capacitor.

As a sensitive element in the invention, a coplanar capacitor is used. The electrodes of the capacitor are of coaxial ring form and are located in one surface level. The capacitor is lowered, by use of a special scanner, on the surface of fluoric graphite powder in a predetermined spot within the pallet area.

Dielectric permeability depends, besides fluorine content in powder, on the powder density. In addition, the graphite powder surface, after fluoridation, is not even but rather waving. This caused by powder volume increase in the process of fluoridation. Therefore, it is needed to insert capacitive sensor in powder at ascertain given depth and stabilize the powder density under the electrodes of the flat laid coplanar sensor.

Adjustment and stabilization of the sensor position, relative to the powder in pallet, is executed by the lowering mechanism of the remote measuring transducer together with a sensor on the powder surface and by the weight compensation mechanism of the transducer when it is inserted into the powder.

Due to uneven fluoridation process within the pallet fluoridation magnitude of graphite powder varies across the pallet. There might be spots of gray color where fluorine content is not sufficient, area of white color with high fluorine content and areas where fluorine content decreases in the deeper powder layers.

In the event of unbalanced (uncompensated) weight of the remote measuring transducer powder CFx under the flat surface of the capacitive transducer turns into highly compressed matter. And the near surface powder layer, due to its electric self-conductance, shields the capacitive transducer electric field. To avoid this shielding effect it is needed to compensate the weight of the remote measuring transducer. This ensures inserting the transducer at the proper depth, stabilizing power density under the working surface of capacitive sensor as well as power conductance.

In the testing process, time dependencies of transducer capacitance and Q-factor are measured and recorded, while the transducer is being inserted. The starting point of transducer inserting into powder is determined at the moment of shifting from the value of constant transducer capacitance to the moment of its linear increasing. The end of inserting is determined by the condition of balance of uncompensated weight of remote measuring transducer and powder resistance. The informative signal is dielectric permeability of fluorocarbon powder. Its value is determined in the end of inserting process.

If sensor field is shielded by powdered material tested the transducer capacitance increases rapidly, which results in increasing of transducer Q-factor. In this case fluorine content in a given area is not recorded.

In some pallet sections the powder thickness might be lower the permissible one for measuring. In this event the metallic bottom of the pallet begins affecting the magnitude of information signal. The effect of the pallet metal bottom leads to sharp increase in transducer capacitance in the process of inserting the transducer. This happens when the working transducer surface with electrodes approaches the pallet bottom, which results in transducer Q-factor decreasing.

To ascertain the pallet bottom effect on the transducer capacitance in the process of its inserting in powder, measurements of time dependence of transducer capacitance are made. To determine the effect of the bottom pallet is measured numerical value capacity during of an immersion of the transducer in the powder. The results of the measurements at 75% of the covered ways until the end of the immersion sensor extrapolated of a special program. Then the results obtained from three-fourths of the distance covered, before the end of inserting sensor, are extrapolated of a special program. Difference between the measured capacitance in the last fourth of the total distance and the extrapolated capacitance values is calculated and compared with the threshold adopted. If the difference is over the threshold and the sensor Q-factor is decreasing in the insertion process the result of measurement of fluorine content in a given area is not recorded.

When there is no shielding effect and the pallet bottom impact is not detected, fluorine content in the testing section is registered by the values of dielectric powder permeability, after the measuring transducer has been fully inserted in the powder.

After the first measurement, the sensor is raised again above the surface of the powder material. Then measurements are made in other sections on the surface of the powdered material. contained in the pallet, and average values are computed. The number of measurements is determined in the process of automatic control system performance. The powdered material quality is determined by the average value of information signal.

Figure 2:
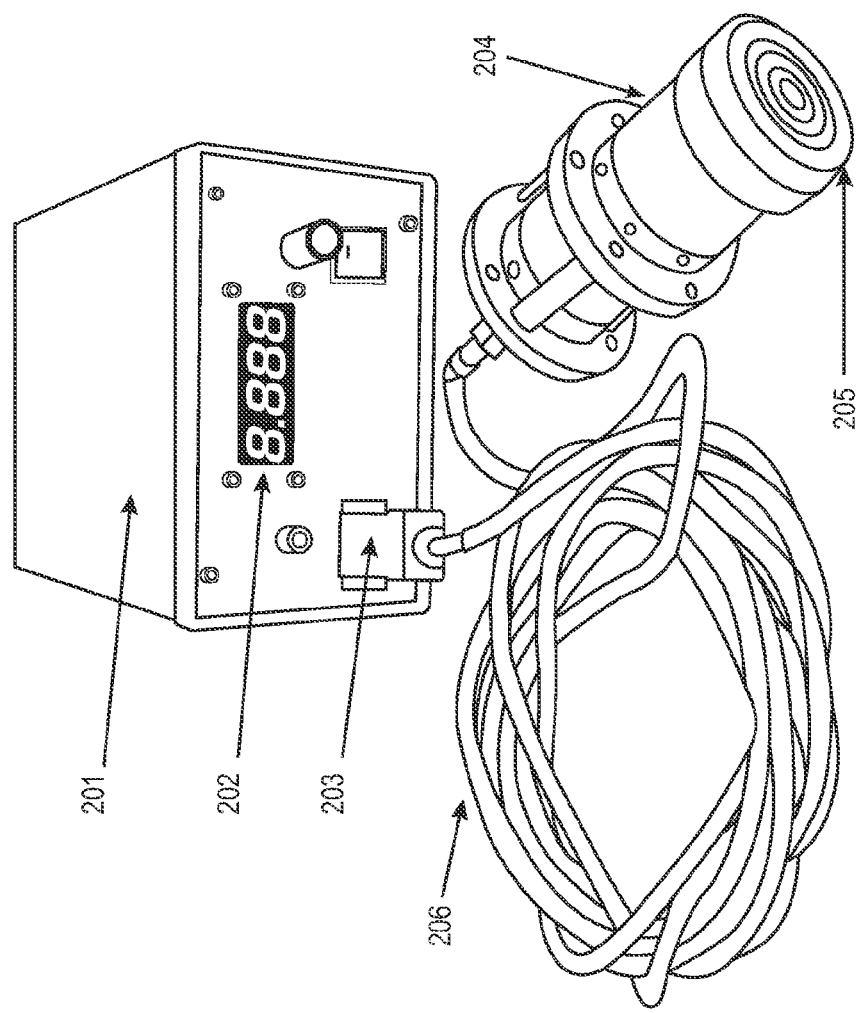
FIG. 2 shows device and transducer, which consist of as following: 201 is the device case; 202 is the display (monitor); 203 is the receptacle for connecting cable; 204 is the remote measuring transducer; 205 is the sensor metal rings in the primary transducer; 206 is the cable for connecting primary transducer to the device.

The design and fundamental operational rules of the measuring block and remote measuring transducer are as follows. The measuring block and remote measuring transducer are intended to determine the percentage of fluorine content in fluoridated graphite powder. General view of the measuring block (MB) and remote (remote?) measuring transducer (RMT) 204 is shown in FIG. 2. is mounted in a rectangular case 201, on the front panel of which there are a monitor (display) 202, control switches, indicators and socket for connecting multiple cable 203 to contact with RMT 204.

On the back panel there are sockets for connecting to alternating current outlets 110V, 60 Hz, grounding terminal and a fuse. RMT (FIG. 3) is a cylindrical case 301 to be used for fastening RMT to the mechanism for lowering-raising scanner. In the RMT edge there is a sensor 205 mounted, which directly interacts with powder. Signal from RMT is transmitted via cable 206 to MB. In MB the signal is converted to digital code shown on the MB monitor in the format PXX.X, where P symbolizes "%" and XX.X indicate numeric values of CFx content, e.g. 48.5.

Signal from RMT is communicated via cable to measuring unit in which its value is converted to digital code shown on display of the measuring unit in PXX.X format, where P corresponds to "%" symbol, XX.X symbols signifying numeric value of the measured fluorine content $C_{Fr}$, for example, 48.5.

Lowering-raising mechanism operates so as to automatically provide fixed pressure applied by sensor's working surface to powder layer. Thus equal conditions for measurements at different spots of the pan are ensured. This, in turn, ensures credibility and accuracy of measurement results. Fixed pressure is generated by using a half-free bob in RMT's lowering-raising mechanism, so that its weight is partially compensated by a counterweight which consists of a number of weights. Required pressure is achieved by adding or taking off counterweight weights.

The diagram of automatic system for determining fluorine content in fluoric graphite powder is shown in FIG. 1 and consists of: 101—scanner to move remote measuring transducer 103 on the horizontal surface and for lowering it onto the powder in the pallet 102; 104—measuring generator, using a capacitive sensor as a resonance circuit, and a base generator, which is identical to the measuring one. Output (Outgoing) signal from the measuring generator is transmitted to block measuring Q-factor 105 of resonance circuit with a capacitive sensor and also to frequency subtraction block 106 of the measuring and base generator 107 reference generator; output signal from the base generator is transmitted to the second receptacle of the frequency subtraction block. 109, 110—two analog-digital transducers; 111—block for identifying extramal point of dependence of capacitive sensor capacitance upon time; block for comparative analysis of resonance circuit Q-factor of the measuring auto generator and capacitance of capacitive sensor; 113—block for extrapolation of time dependence of capacity of capacitive sensor at the moment when it is inserted into powder; 115—block for computing the difference between the factual and extrapolated values of capacity of capacitive sensor while the sensor is being inserted into powder; 116—block for comparison of present difference with "threshold"; 112—calibration block; 117—registration block.

Measuring and base generators, Q-factor measuring block and frequency subtraction block are parts of RMT 103, which is fastened jn the scanner frame. The input jack of the first analog-digital transducer is connected to frequency subtraction block of the remote measuring transducer. Output jack of the first transducer is connected parallel to block of comparative analysis 111, calibration block 112, block for identifying extramal point of dependence of capacitive sensor capacitance upon time 113; extrapolation block 114 and difference computing block 108.

Block for identifying extramal point, which generates signal that corresponds to the beginning of remote transducer inserting into powder, is linked to block of comparative analysis, calibration and extrapolation blocks and block for computing difference of a special computing device.

The signal on the end of transducer inserting in powder 118 is generated by the element of vertical shifting of the scanner frame. This signal is transmitted to extrapolation block, block for computing difference and registration block.

Input jacks of block for computing difference are connected to output jack of the first analog-digital transducer and output of extrapolation block. Output jack of block for computing difference is connected to threshold comparison block. Output jack of threshold comparison block is connected to calibration block control input.

To make measurements, RMT 401 is positioned over powder's surface in the pallet, using electric drives 402, 404 designed for transporting the platform on which it is mounted. Then RMT is lowered onto powder's layer using a special driving-gear which also has its own electric drive 403

The scanner operates in this way. RMT is positioned by an operator at a given spot over powder. The positioning is executed by electrical signals to the electric drive for horizontal transporting. The signals are generated in an electronic block controlling the scanner. Then the operator starts the lowering-raising mechanism. RMT is placed on powder and is moving inside towards the pallet bottom.

Lowering-lifting mechanism is designed in such a way that as the immersion RMT flat surface the pressure sensitive element located at the end of the shell RMT, is gradually offset by the increasing power of resistance medium powder. When these forces are equal, RMT stops. This RMT is submerged in a layer porolubinu 303. The design of the mechanism of lowering-lifting ensures that the depth will be sufficient to correct the measurement values of CFx. It will not depend on variations in the thickness of the layer of powder on a pallet.

Figure 3:
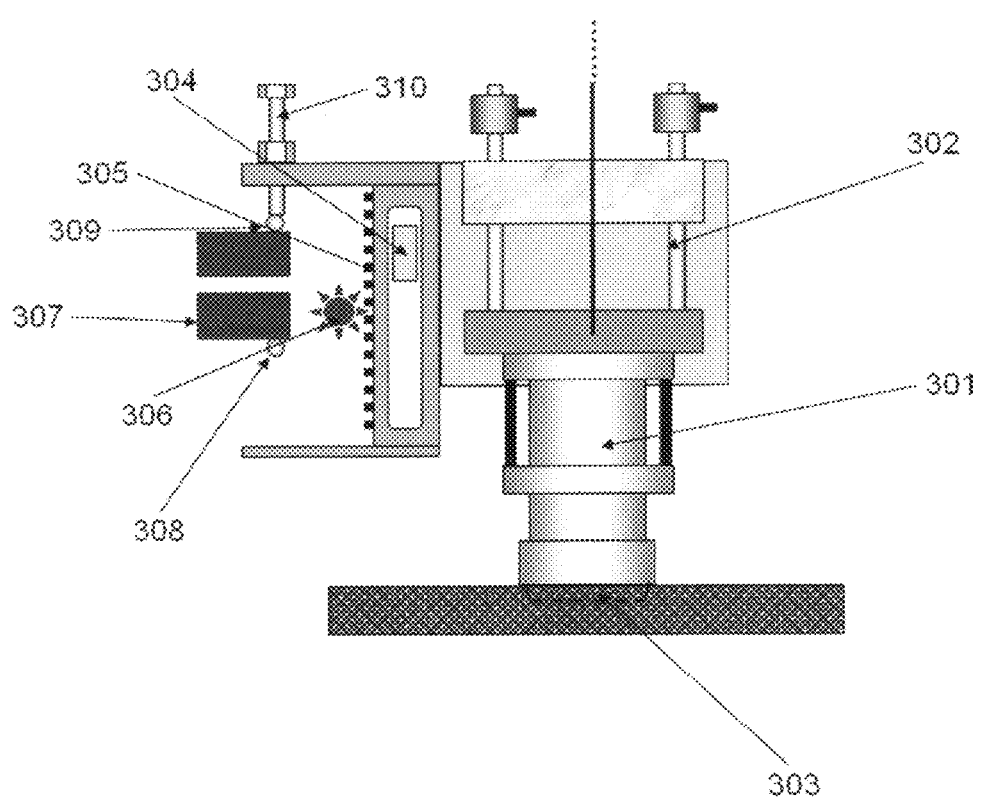
FIG. 3 shows the remote primary transducer with a block for mounting on scanner where 301 is the primary transducer; 302 is the block for attaching transducer to scanner; 303 is the depth of inserting sensor in powdered material; 304 is the slide-block; 305 is the rack; 306 is the gear; 307 is the lower shelf of cramp; 308 is the lower edge switch; 309 is the upper edge switch; 310 is the adjusting bolt.
Figure 4:
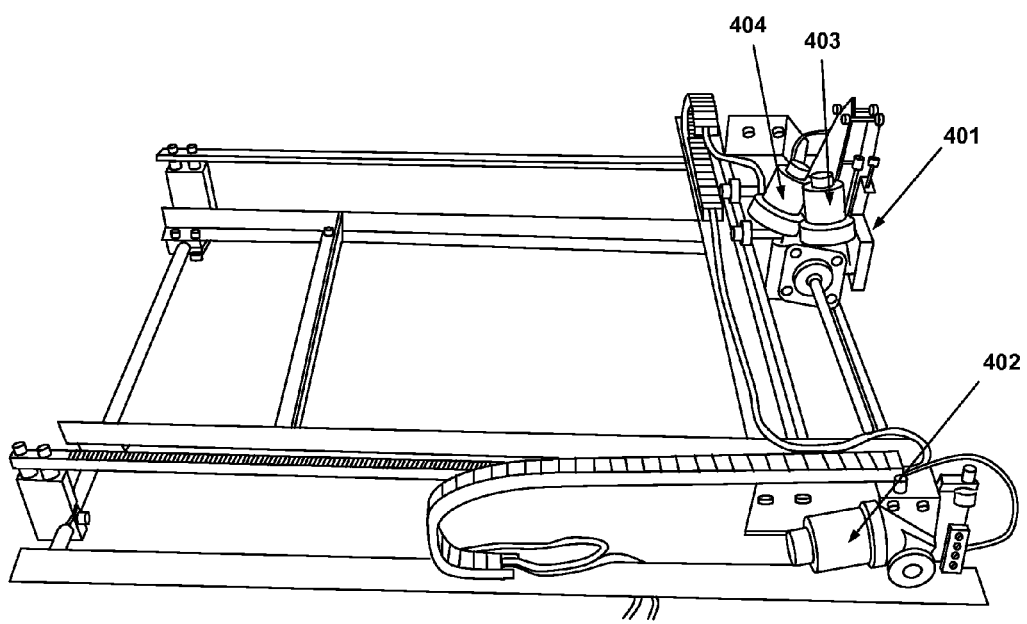
FIG. 4 presents the scanner general view where: 401 is the remote primary transducer; 402 and 404 are electric drives for moving scanner platform; 403 is the electric drive for lowering and raising primary transducer.
Figure 5:
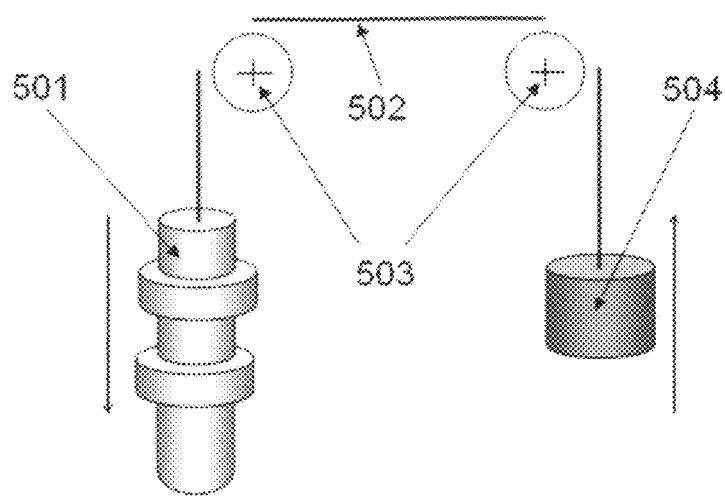
FIG. 5 illustrates the diagram of interaction of remote primary transducer and counterweight: 501 is the remote primary transducer; 502 is the cable for connecting remote primary transducer and counterweight; 503 is the items for fastening primary transducer and counterweight; 504 is the counterweight.

To achieve this objective in the design of the lifting-lowering applied semi-free pendant (half-free bob) RMT in this case a partial compensation of its own weight, together with the weight of his attachment to the mechanism. Compensation weight RMT 501, together with its fastening elements 503 is implemented counterweight 504. Counterweight fixed total tether 502. Transferred through the cable reels 503. The compensation is partial. That's why the RMT applies a force equal to the difference between the weight of RMT to the elements and forces mounting tension cable 502. This aims to bring the power of suspension in the movement indicated by arrows in FIG. 5. Mutual location of RMT layer of powder in the pan, and other details of the mechanism of lowering-lifting is shown in FIG. 3.

Total weight RMT, bracket and rod with the striker is only partially compensated by tension cable 502. Therefore, in the initial state RMT is "hanging." The platform with fixed on it RMT can move vertically in the crosshead slide-block 304. To this end, rack 305 is connected to gear 306. Pinion rotates motorized vertical movement of 403. When the platform reaches the uppermost and the lower shelf bracket 307 presses the lower limit switch 308. This leads to the exclusion of vertical electric displacement. RMT is fixed in the up position When the operator includes the electric displacement in the direction the vertical lifting-lowering the mechanism for lowering starts to read. Pinion 306 starts to rotate electrically. The platform starts to descend. Lowering will continue until the work is not an upper limit switch 309. The switch is included by clicking screw 310. Screw fixed lock-nut on top of a shelf bracket. After the plane touches the surface of a powder sensitive element, RMT continues to move, and sinking into the layer of powder. As the RMT starts to move the resistance medium powder increases. This is due to the fact that the powder under the sensitive element RMT compacted. When immersing the RMT in the powder at the desired depth of the resistance becomes equal weight RTM compensated with a fixture. The movement of the RMT down stops (FIG. 3).

At this phase of the movement of RMT is immersed in a layer of powder. By the time of operation the upper limit switch RMT becomes completely motionless. It is therefore necessary free travel of the platform. Readout from the display unit of measurement should be made only after full stop Full stop of the platform occurs when pressure of the screw push to the upper limit switch.

EXAMPLES

Example 1

Figure 6:
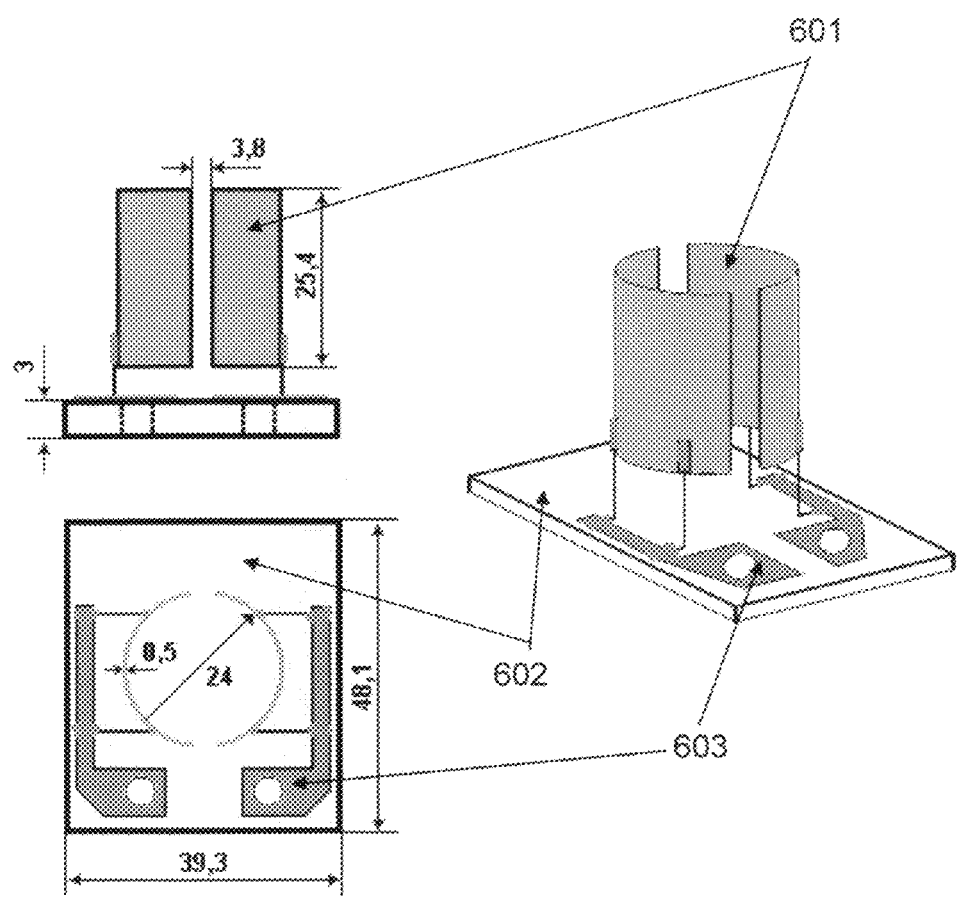
FIG. 6 presents the capacitive primary transducer design for evaluation the fluorocarbon powders placed inside a glass (beaker) where: 601 is the capacitor plates; 602 is the glass-fiber plastic base; 603 is the connecting terminals.

In Example 1 the results of the evaluation the powder, poured into glass vessels (cups, test tubes) are presented. Sensor for the investigation is presented in FIG. 6

The samples of CFx with the different levels of fluorination were evaluated as shown below. Capacitor plates 601 (FIG. 6.) were made of copper. The base cup is made of glass tekstolita 602. The findings of the terminals and connecting wires are made of copper 603. The research was carried out at frequencies f=50 MHz and 70 MHz. The results are presented in Tables 1, 2. As an informative parameter in these measurements were Q factor the capacitance were used.

TABLE 1

Investigation of dielectric characteristics CFx powders with different content of fluorine. Measurements conducted at a frequency f = 50 MHz. The initial parameters of the resonant circuit with transducer without tube were:
$Q_0 = 198, C_0 = 110.12$ pF

| Noo samples | CFx, % | $Q_1$ | $C_1$, pF | $Q_{1p}$ | $C_{1p}$, pF | $\delta C_1$, pF | $\delta C_{1p}$, pF |
|---|---|---|---|---|---|---|---|
| 1 | 0 | 96 | 100.20 | 113 | 99.36 | 9.92 | 10.76 |
| 2 | 10.66 | 194 | 107.44 | 192 | 107.17 | 2.68 | 2.95 |
| 3 | 17.26 | 193 | 107.80 | 192.5 | 107.39 | 2.32 | 2.73 |
| 4 |  | 192.5 | 108.30 | 192.5 | 108.10 | 1.82 | 2.02 |
| 5 | 39.81 | 192.5 | 108.51 | 192.5 | 108.33 | 1.61 | 1.79 |
| 6 |  | 192.5 | 108.72 | 195 | 108.57 | 1.40 | 1.55 |
| 7 | 48.99 | 195.5 | 108.68 | 195.5 | 108.60 | 1.44 | 1.52 |
| 8 | 58.12 | 196 | 109.12 | 195.5 | 109.10 | 1.0 | 1.02 |

The index "p" indicates that the powder was subjected to vibration compaction and maximize sealed in this way. The amount of change capacitance $\delta C_1 = C_0 - C_1$. The concentration of fluoride in the powder pre-determined chemical means. It should be noted, and significantly decrease the value $\delta C_1$ monotonically with increasing concentration of fluoride in the powder

TABLE 2

Investigation of dielectric characteristics CFx powders with different content of fluorine. Measurements conducted at a frequency f = 70 MHz. The initial parameters of the resonant circuit with transducer without tube were: $Q_0 = 208$, $C_0 = 53.09$ pF

| No sample | CFx, % | $Q_1$ | $C_1$, pF | $Q_{1p}$ | $C_{1p}$, pF | $\delta C_1$, pF | $\delta C_{1p}$, pF |
|---|---|---|---|---|---|---|---|
| 1 | 0 | 50 | 42.48 | 78 | 42.46 | 10.61 | 10.63 |
| 2 | 10.66 | 200.5 | 50.22 | 200.5 | 50.07 | 2.87 | 3.02 |
| 3 | 17.26 | 201.5 | 50.78 | 201.5 | 50.50 | 2.31 | 2.59 |
| 4 | ? | 203 | 51.44 | 202.5 | 51.29 | 1.65 | 1.80 |
| 5 | 39.81 | 204.5 | 51.57 | 204 | 51.36 | 1.52 | 1.73 |
| 6 | ? | 209 | 51.69 | 209 | 51.66 | 1.40 | 1.43 |
| 7 | 48.99 | 209.5 | 51.68 | 209.5 | 51.60 | 1.41 | 1.49 |
| 8 | 58.12 | 209.5 | 52.20 | 209.5 | 52.10 | 0.89 | 0.99 |

It should be noted monotonically increasing Q-factor of the capacitive sensor with an increase of the level of fluoride in the powder. Previously at a frequency of 50 MHz pattern of reducing the value $\delta C_1$ with increasing concentration of fluoride in the powder is observed here and at a frequency of 70 MHz. Graphs change the capacitance of the sensor depending on the content of fluorine in the powder for different frequencies of the probing electric field are shown in FIGS. (7, 8). Given that in this case, the measurement of dielectric properties of the powder is carried out through the glass tubes, high-value of the capacitance for powder carbon with a zero fluorine content does not mean high value of permittivity of the powder.

Figure 7:
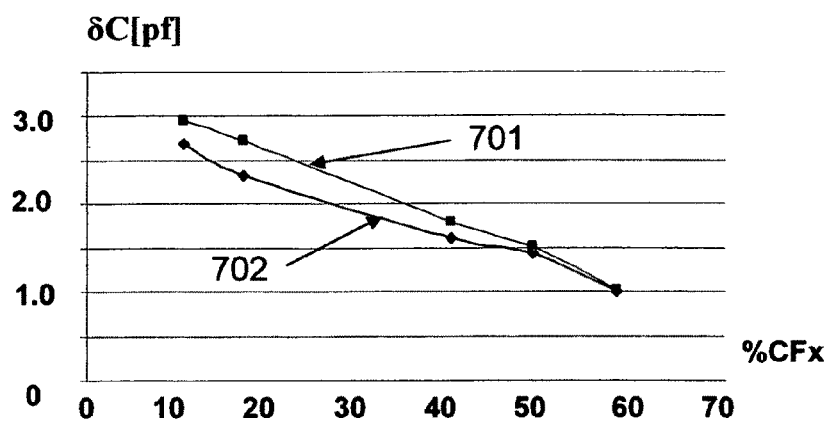
FIG. 7 illustrates the change of capacitance of electric capacitive sensor when fluorine content is increased in the powder CFx: 701 is the capacitance change ($\delta C_{1p}$) for condensed powder; 702 is the capacitance change ($\delta C_{1p}$) for non-condensed powder. Data on powder not containing fluorine (initial non-fluorided carbon) are not shown on the graph Measuring frequency is 50 MHz.
Figure 8:
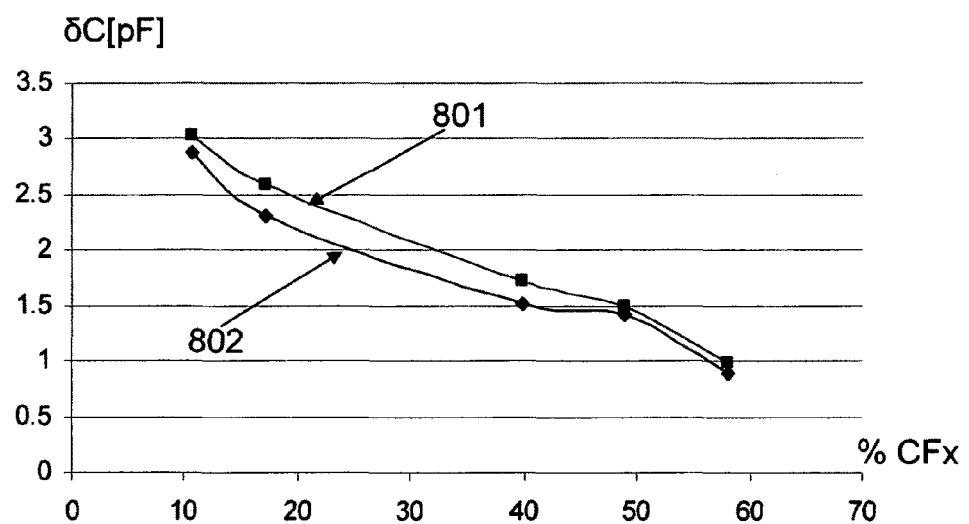
FIG. 8 illustrates the change of capacitance of capacitive transducer when fluorine content is increased in the powder CFx: 801 is the capacitance change ($\delta C_{1p}$), for condensed powder; 802 is the capacitance change ($\delta C_{1p}$) for non-condensed powder. Data on powder not containing fluorine (initial non-fluorided carbon) are not shown on the graph. Measuring frequency is 70 MHz

The main result to be presented at FIGS. 7, 8 schedule is monotonically changing the capacitance of the sensor with increased concentrations of fluoride in the powder. This pattern is repeated for the unconsolidated and the compacted powder samples. This is very significant is that the change in capacitance of the sensor is significant—with increasing concentrations of fluoride from 10.66% to 58.12% paid capacitance of the sensor $\delta C_1$ reduced to approximately three times, with approximately 3 to 1 pF.

Example 2

This example shows the results of a study of powders using coplanar ring multiple sensors. (FIG. 2. 205). Developed, produced and applied in the course of studies was electric-capacitive sensor with a laid on coplanar electrodes. Electrode shape may be either round or right-angled at that. It was ascertained for right-angled electrodes, significant concentration of electric-field strain occurs in the corners. This flaw is absent in the round construction.

The distance between the main electrodes of the electro capacitance sensor is selected equal to 2 mm. A small gap reduces the working capacity, but increases the depth of electric field sensing powder converter The method of measurement was as follows. Recorded the own options parameters of the transducer ($Q_0$, $C_0$) at a working frequency. Then the sensor was installed on the powder layer with the thickness of approximately 10 mm and the measured values of $Q_1$, $C_1$ was conducted. After that on the surface of the powder fell from the plate of Al with the size 54×54 mm and 3 mm thick and $Q_1p$, $C_1$ were fixed. The plate fell on the side opposite to the surface, to simulate the bottom of the pallet. The results of the measurements at frequencies of 50 MHz and 75 MHz are presented n in Tables 3 and 4.

TABLE 3

The results of measurements of dielectric characteristics of powders CFx with the variety level of fluorination. Sensor was used with the caplanar electrodes (FIG. 2-205). The measurements were carried at the frequency f = 50 MHz. Own parameters of the sensor were: $Q_0 = 161$, $C_0 = 107.79$ pF, $\gamma$, is the relative error in the measurement of capacitance in % of the average of the pallet

| No samples | CFx, % | $Q_1$ | $C_1$, pF | $Q_{1p}$ | $C_{1p}$, pF | $\delta C_1$, pF | $\delta C_{1p}$, pF | $\gamma$, % |
|---|---|---|---|---|---|---|---|---|
| 1 | 0 | | | | | | | |
| 2 | 10.66 | 159 | 100.95 | 159 | 100.24 | 6.84 | 7.55 | 10.3 |
| 3 | 17.26 | 159.5 | 101.64 | 159.5 | 101.21 | 6.15 | 6.58 | 7.0 |
| 4 | ? | 160 | 103.51 | 160 | 103.32 | 4.28 | 4.47 | 4.4 |
| 5 | 39.81 | 160 | 104.12 | 160 | 103.91 | 3.67 | 3.88 | 5.7 |
| 6 | ? | 160.5 | 105.12 | 160.5 | 104.96 | 2.67 | 2.83 | 6.0 |
| 7 | 48.99 | 162 | 105 | 162 | 104.76 | 2.79 | 3.03 | 8.6 |
| 8 | 58.12 | 163 | 107.16 | 163 | 107.05 | 0.63 | 0.74 | 17.5 |

TABLE 4

The results of measurements of dielectric characteristics of powders CFx with the variety level of fluorination. Sensor was used with the caplanar electrodes (FIG. 2-205). The measurements were carried at the frequency f = 75 MHz. Own parameters of the sensor were: $Q_0 = 148$, $C_0 = 42.36$ pF; $\gamma$, is the relative error in the measurement of capacitance in % of the average of the pallet

| No samples | CFx, % | $Q_1$ | $C_1$, pF | $Q_{1p}$ | $C_{1p}$, pF | $\delta C_1$, pF | $\delta C_{1p}$, pF | $\gamma$, % |
|---|---|---|---|---|---|---|---|---|
| 1 | 0 | | | | | | | |
| 2 | 10.66 | 132 | 33.50 | 132 | 33.29 | 8.86 | 9.18 | 3.6 |
| 3 | 17.26 | 135 | 34.92 | 134 | 34.5 | 8.08 | 8.42 | 4.2 |
| 4 | ? | 142 | 38.04 | 142 | 37.82 | 4.32 | 4.54 | 5.1 |
| 5 | 39.81 | 142 | 38.28 | 141 | 38.05 | 4.08 | 4.31 | 5.6 |
| 6 | ? | 144 | 39.39 | 144 | 39.22 | 2.97 | 3.14 | 5.7 |

TABLE 4-continued

The results of measurements of dielectric characteristics of powders CFx with the variety level of fluorination. Sensor was used with the caplanar electrodes (FIG. 2-205). The measurements were carried at the frequency f = 75 MHz. Own parameters of the sensor were: $Q_0$ = 148, $C_0$ = 42.36 pF; $\gamma$, is the relative error in the measurement of capacitance in % of the average of the pallet

| No samples | CFx, % | $Q_1$ | $C_1$, pF | $Q_{1p}$ | $C_{1p}$, pF | $\delta C_1$, pF | $\delta C_{1p}$, pF | $\gamma$, % |
|---|---|---|---|---|---|---|---|---|
| 7 | 48.99 | 144 | 39.45 | 144 | 39.22 | 2.91 | 3.14 | 7.9 |
| 8 | 58.12 | 147 | 41.52 | 147 | 41.42 | 0.84 | 0.94 | 11.9 |

The value of $\gamma$ is defined as:

$$\gamma,\% = 100(\delta C_{1p} - \delta C_1)/\delta C_1 \qquad (1)$$

Figure 9:
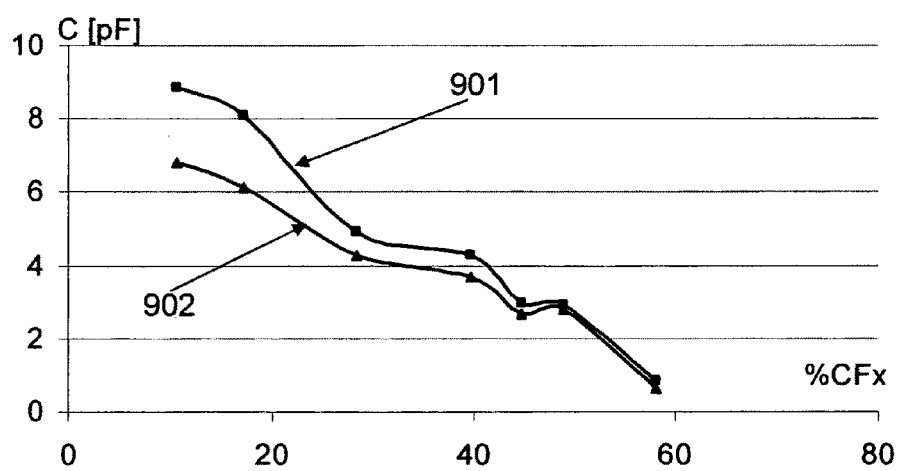
FIG. 9 illustrates the dependence of capacitance of capacitive transducer on fluorine content in powder CFx, measured at frequencies f=50 MHµz and f=75 MHz. Data on powder not containing fluorine (initial non-fluorided carbon) are not shown on the graph; 901 is under working frequency 75 MHz; 902 is under working frequency 50 MHz.

Dependences of the value of capacity changes $\delta C_1$ of the content of fluorine in the powder CFx according to the data of Tables 3 and 4 are shown in graphs in FIG. 9.

These graphics are dull and downward to show a significant (6-8 pF) capacitance change of the sensor with an increase of fluoride in the powder CFx from 10.66 to 58.12%. A large amount of information signal ($\delta C_1$) shows that the use electro capacitance method for quality control of fluorinated graphite powder in the pallet provide a positive results.

Example 3

In this Example the results of determining the value of the measurement error depending on the content (%) of fluorine in the fluorinated carbon are presented. Testing was conducted in the production conditions.

Taking into consideration the volume of tests of fluorinated graphite powder, a pallet for powder was manufactured. The pallet was represented by a metal case approximately 18×18 cm, height of its walls 17-18 mm, its bottom being made of rigid paper. Using a special spoon, one placed powder into the pallet, as evenly as possible. Then the filled-up pallet was set on an empty pan in the place suitable for measurement. Powder level in the pallet amounted to 12-17 mm. Powder surface in the pallet was not leveled using any kind of tool, pallet with powder was carried to the pan without shaking.

Figure 10:
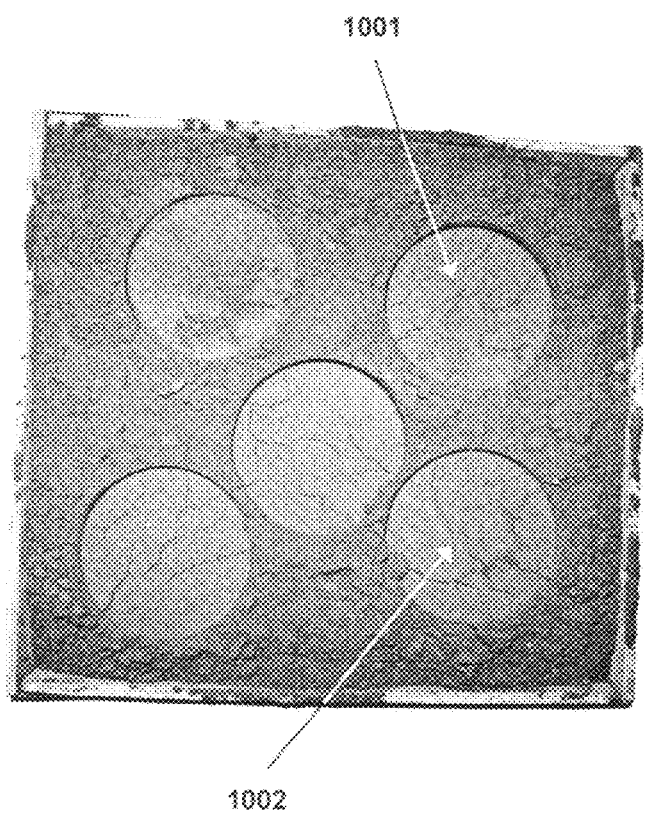
FIG. 10 presents the photo of powder CFx surface in pallet for powder as it looks after measurements: 101 are the traces remained after measurements; 102 are the cracks on the flat bottom of the depression.

The measuring transducer was positioned over the powder. Measurement was executed by way of lowering the measuring transducer onto the powder and taking subtractions according to the device's scale after the measuring transducer was finally set up. To eliminate influence of the edge effect, distance between side surface of the measuring transducer and the side wall of the pallet with powder should be at least 25 mm. So, without overlapping of control spots of the measuring transducer on powder surface within the pallet with powder, one could execute, as a rule, 5-6 measurements at most. Measurement results are included in Tables No. 5-9 below. Measurements were conducted in the following way:

Powder being tested was placed in a prepared flat pallet, its bottom made of a dielectric material Pallet with powder was set onto the pallet Using a manufactured device, one measured physical parameters of the transducer that was lowered onto the powder. Measurements were made within 5—six circles across powder surface (FIG. 10).

Powder was transferred to the pallet and mixed up thoroughly

Part of the mixed up powder was subjected to chemical analysis

The rest of the powder was placed in a flat pallet, and then physical parameters of powder were measured, as described above.

TABLE 5

Measurement results for powder No 1.

| $C_F$, initial chemical analysis | $C_F$, repeatedly | | Results of physical parameters measurements, $U_i$ | | | | | |
|---|---|---|---|---|---|---|---|---|
| | $C_F(1)$ Chemical analysis after powder mixing | $C_F(2)$ Chemical analysis after powder mixing | $U_1$ | $U_2$ | $U_3$ | $U_4$ | $U_5$ | $U_6$ |
| 23 | 25.39 | 25.71 | | | | | | |
| | Without mixing | | 42.8 | 43.4 | 42.3 | 44.3 | 43.3 | — |
| | | | 41.2 | 41.6 | 41.9 | 44.8 | 43.7 | 45.1 |
| | | | 45.0 | 44.6 | 43.7 | 47.0 | 44.9 | — |
| | $U_{average}$, $\sigma$, $\gamma$ % | | $U_{average}$ = 43.73, $\sigma$ = 1.533, $\gamma$ = 3.51% | | | | | |
| | After mixing | | 44.7 | 45.2 | 43.9 | 44.2 | 44.6 | — |
| | $U_{average}$, $\sigma$, $\gamma$ % | | $U_{average}$ = 44.52, $\sigma$ = 0.376, $\gamma$ = 0.84% | | | | | |

The significance of the relative error was calculated by the formula:

$$\gamma = \sigma/U_{average}, \%.$$

Data relating to each line of section "Without mixing" was obtained for every single time that pallet for powder was filled up with powder from the polyethylene bag in which sample No. 1 was kept, without mixing the powder. As follows from table 5, average value increased by 1.8% after thorough mixing of powder in the polyethylene jar, whereas standard deviation $\sigma$ and relative root-mean-square error $\gamma$ that characterize degree of dispersion of measurement results in relation to the average value, both decreased by approximately 4 times.

TABLE 6

Measurement results for powder No. 2.

| $C_F$, initial chemical analysis | $C_F$, repeatedly | | Results of physical parameters measurements, $U_i$ | | | | | |
|---|---|---|---|---|---|---|---|---|
| | $C_F(1)$ Chemical analysis after powder mixing | $C_F(2)$ Chemical analysis after powder mixing | $U_1$ | $U_2$ | $U_3$ | $U_4$ | $U_5$ | $U_6$ |
| 44 | 38.78 | 39.89 | | | | | | |
| | Without mixing | | 58.1 | 60.7 | 57.9 | 60.0 | 60.9 | — |
| | $U_{average}, \sigma, \gamma \%$ | | $U_{average} = 59.52, \sigma = 1.216, \gamma = 2.04\%$ | | | | | |
| | After first mixing | | 63.2 | 63.1 | 62.3 | 63.4 | 62.7 | — |
| | $U_{average}, \sigma, \gamma \%$ | | $U_{average} = 62.94, \sigma = 0.352, \gamma = 0.56\%$ | | | | | |
| | After second mixing | | 63.7 | 62.9 | 63.4 | 63.6 | 63.4 | — |
| | $U_{average}, \sigma, \gamma \%$ | | $U_{average} = 63.4, \sigma = 0.20, \gamma = 0.315\%$ | | | | | |

As follows from table 6, after thorough mixing of powder, average value increased by 5.9% Standard deviation $\sigma$ and relative root-mean-square error $\gamma$ decreased by approximately 3.5 times after the first mixing. After the powder which was previously thoroughly mixed was mixed for the second time in the jar, average value increased by 0.7%, whereas standard deviation $\sigma$ and relative root-mean-square error $\gamma$ decreased additionally by 1.77 times. Increase in average value by 0.7% after the second mixing is apparently connected with its fluctuations due to small quantity of measurements (5 measurements within the pallet for powder). As for $\sigma$ and $\gamma$ having dropped by 1.77 times, this fact means that the mixing procedure must be long and, apparently, it must be executed in several steps.

FIG. 10 shows a snap-shot of no. 2 pallet with powder as it looks after measurements. In the picture, one can clearly see traces remaining after measurements, including cracks on the flat bottom of the depression. This makes the impression that powder no. 2 has higher temperature. To check this hypothesis, this powder was dried in an oven for several hours. Measurement results obtained after drying are shown in Table 8.

TABLE 7

Measurement results for powder No. 2 after drying

| $C_F$, initial chemical analysis | $C_F$, repeatedly | | Results of physical parameters measurements, $U_i$ | | | | | |
|---|---|---|---|---|---|---|---|---|
| | $C_F(1)$ Chemical analysis after powder mixing | $C_F(2)$ Chemical analysis after powder mixing | $U_1$ | $U_2$ | $U_3$ | $U_4$ | $U_5$ | $U_6$ |
| 44 | 38.78 | 39.89 | | | | | | |
| | Without mixing | | 62.0 | 63.0 | 62.4 | 62.4 | 62.3 | — |
| | $U_{average}, \sigma, \gamma \%$ | | $U_{average} = 62.42, \sigma = 0.232, \gamma = 0.37\%$ | | | | | |
| | After mixing | | 63.3 | 63.4 | 63.0 | 62.4 | 63.0 | — |
| | $U_{average}, \sigma, \gamma \%$ | | $U_{average} = 63.02, \sigma = 0.264, \gamma = 0.42\%$ | | | | | |

By comparing data from table 6 and 7, one can state that average value showed very little change, if any. Meanwhile, comparing the respective values of σ and γ in table 7 for variants with no mixing and after mixing, one should note that mixing had very little effect upon dispersion of measurement results, if any. Apparently, dry powder yields to mixing much better and produces homogeneous mixture easily enough.

However, while standard deviation of measurement results after first mixing decreased approximately by 3.5 times for powder before drying, dropping 1.8 times further after second mixing, mixing after drying had no effect upon measurement results dispersion. Hence, powder's humidity slightly decreasing causes powder to produce homogeneous mixture significantly easier.

TABLE 8

Measurement results for powder No. 3.

| $C_F$, initial chemical analysis | $C_F$, repeatedly | | Results of physical parameters measurements, $U_i$ | | | | | |
|---|---|---|---|---|---|---|---|---|
| | $C_F(1)$ Chemical analysis after powder mixing | $C_F(2)$ Chemical analysis after powder mixing | $U_1$ | $U_2$ | $U_3$ | $U_4$ | $U_5$ | $U_6$ |
| 45 | 46.53 | 46.88 | | | | | | |
| Without mixing | | | 61.7 | 61.3 | 61.4 | 61.5 | 61.2 | — |
| $U_{average}$, σ, γ % | | | $U_{average}$ = 61.42, σ = 0.144, γ = 0.23% | | | | | |
| After mixing | | | 60.8 | 61.3 | 61.0 | 61.4 | 61.3 | — |
| $U_{average}$, σ, γ % | | | $U_{average}$ = 61.16, σ = 0.208, γ = 0.34% | | | | | |

It is evident from table 8, after thorough mixing of powder, average value dropped by 0.4%. Standard deviation σ and relative root-mean-square γ rose approximately by 1.4 times after mixing. Absolute values of root-mean-square errors are quite small at that. Therefore, increase of σ and γ after mixing can be attributed to faults of experiment. However, it should be noted that for fluorine concentration $C_F$=45%, dispersion of measurement results for measurements within pallet for powder is quite insignificant also in case of no mixing. Thus, one can state that if $C_F$=45%, there is no need in mixing of fluorinated graphite powder.

TABLE 9

Values of relative root-mean-square deviations for powders with no mixing

| | Number of sample, $CFx_{initial}$, % | | |
|---|---|---|---|
| Value of σ | #1, | #2 | #3 |
| $Y_{i, (without\ mixing)}$, % | 23% | 44% | 45% |
| | 3.5 | 0.37 | 0.23 |

One can see from data of Table 9 that, beginning from concentration $C_F$=44%, values of relative root-mean-square deviations go down drastically, and mixing of powders is not so significant as for low-fluorine-content powders (up to and including 39%). Correlations of standard deviations of measurement results for powders with various fluorine content before and after mixing are different by several times. However, after mixing, measurement results dispersion decreases significantly. Meanwhile, absolute values of standard deviations (root-mean-square deviations) for powder with fluorine content of more than 44% are 6-7 times lower, than in fluorine content range from 23 to 36%. Thus, mixing of high fluorine-content powders is not significant, these powders are homogeneous enough, whereas low fluorine-content powders are characterized by significant heterogeneity.

Drying of powder with CF(initial)=44% has demonstrated that average value of measurement results did not change after drying, that is humidity of initial powder was insignificant which was noted by workers of enterprise before drying.

Example 4

In this example, based on the measurement results of samples constructed calibration curves, confirming the high efficiency of the developed method and apparatus for non-destructive testing.

Using average values of signals, one has plotted dependences of $U_{i,average}$ values on fluorine content in powder $C_F$,% which are calibrating characteristics of the apparatus. As $C_F$ values one used average values of two second chemical analyses executed after thorough mixing of each powder in a jar. The calibrating characteristic plotted for $U_{i,average}$ values of powders before mixing is shown on FIG. 11, whereas FIG. 12 shows this characteristic plotted for $U_{i,average}$ values of powders after mixing.

Figure 11:
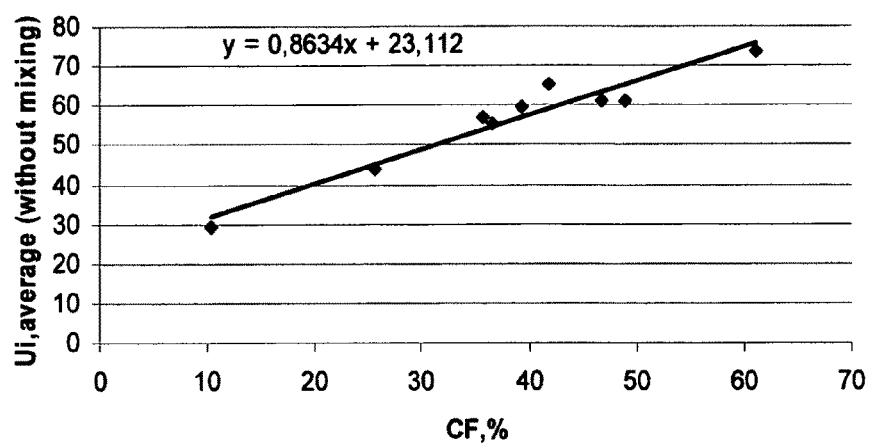
FIG. 11 presents the calibrating characteristics plotted for informative parameter $U_{i,average}$ values of powders before mixing. Correlation coefficient r=0.967.
Figure 12:
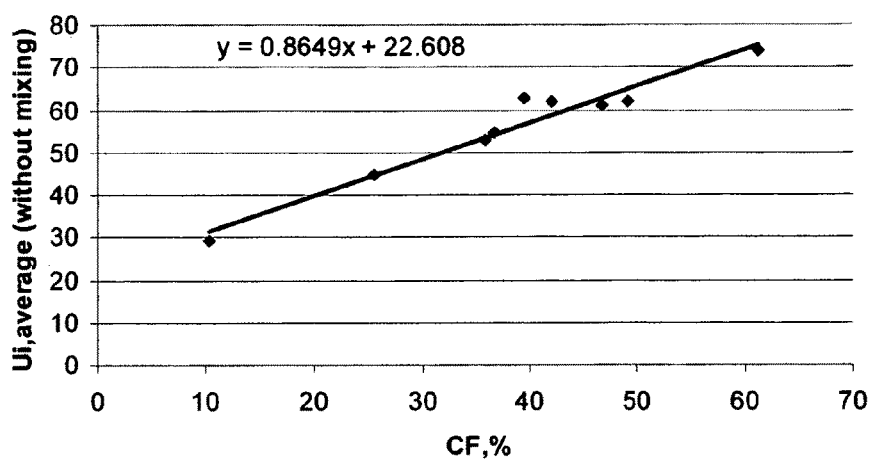
FIG. 12. presents the calibrating characteristics plotted for informative parameter $U_{i,average}$ values of powders after mixing. Correlation coefficient r=0.974.

It is evident from location of points on FIG. 11 and FIG. 12 that the most suitable kind of approximating dependence is a linear dependence. It is evident from the equations that slope of the approximating lines is virtually the same. They differ somewhat (by 2%) in terms of shift along ordinate axis. Correlation coefficient obtained by way of measuring powders after their mixing is somewhat greater.

Apparatus was calibrated in accordance with the dependence averaged-out by FIG. 11 and FIG. 12. After that, figures on its indicator correspond to percent content of fluorine in fluorinated carbon powder.

Example 5

This example shows the results of the tests proposed in the patent, a method and apparatus in the production environment. The tests were carried out directly from thermo reactor on-line at the complex in the pallets. Below the measurement results the level of CFx degree of fluorination for the powder in the pallet are presented. The results were obtained using non-destructive electromagnetic testing device and calibration described above. The goal was to provide the evaluation of the uniform distribution of the level of CFx fluorination on the pallet after synthesis the CFx. Measurement results for fluorinated graphite powder in pallet no. 2 obtained using a calibrated apparatus are shown in Table 10.

TABLE # 10

Measurement results level of CFx degree of fluorination for fluorinated graphite powder in pallet No. 2

| y, cm | x, cm | | | | | |
|---|---|---|---|---|---|---|
| | 36 | 31 | 26 | 21 | 16 | 11 |
| 6 | 62.3 (#6) | 62.4 (#5) | 62.5 (#4) | 62.4 (#3) | 62.3 (#2) | 61.7 (#1) |
| 11 | 62.6 #12 | 62.7 #11 | 62.8 #10 | 62.7 #9 | 62.6 #8 | 62.3 #7 |
| 16 | 62.8 #18 | 62.8 #17 | 62.7 #16 | 62.7 #15 | 62.7 #14 | 62.7 #13 |
| 21 | 62.7 #24 | 62.8 #23 | 62.6 #22 | 62.7 #21 | 62.3 #20 | 62.6 #19 |
| 26 | 62.9 #30 | 62.6 #29 | 62.7 #28 | 62.6 #27 | 62.5 #26 | 62.5 #24 |
| 31 | 62.9 #36 | 62.7 #35 | 61.8 #34 | 62.0 #33 | 61.6 #32 | 61.9 #31 |
| 36 | 63.1 #42 | 62.7 #41 | 62.1 #40 | 61.7 #39 | 61.8 #39 | 61.9 #37 |
| 41 | 62.7 #48 | 61.7 #47 | 59.5 #46 | 60.2 #45 | 58.1 #44 | 58.6 #43 |
| 46 | 62.7 #54 | 61.7 #53 | 60.4 #52 | 59.0 #51 | 52.0 #50 | 57.2 #49 |
| 51 | 62.7 #60 | 61.5 #59 | 58.8 #58 | 57.8 #57 | 57.3 #56 | 57.9 #55 |
| 56 | 62.5 #66 | 61.0 #65 | 57.9 #64 | 56.1 #63 | 55.8 #62 | 55.7 #61 |
| 61 | 62.6 #72 | 61.5 #71 | 58.7 #70 | 55.7 #69 | 56.3 #68 | 59.0 #67 |

It is evident from data shown in table 10, powder in pallet no. 2 is homogeneous enough.

The lowest value of fluorine concentration is observed at points 61, 69 and amounts to $C_F$=55.7%. The greatest value of fluorine concentration is observed at points 30, 36 and amounts to $C_F$=62.9%. In general, shifting in downward and right direction causes reduction of fluorine concentration in fluorinated graphite powder.

Figure 13:
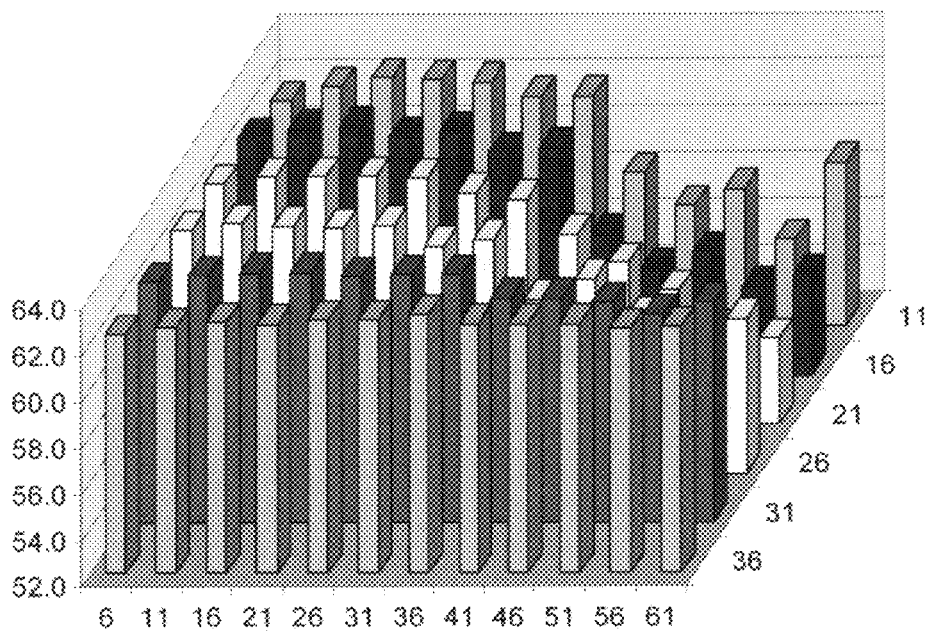
FIG. 13 shows the three-dimensional graph of fluorine-concentration distribution in CFx powder along co-ordinates in the plane of pallet No. 2. after fluorination process.
Figure 14:
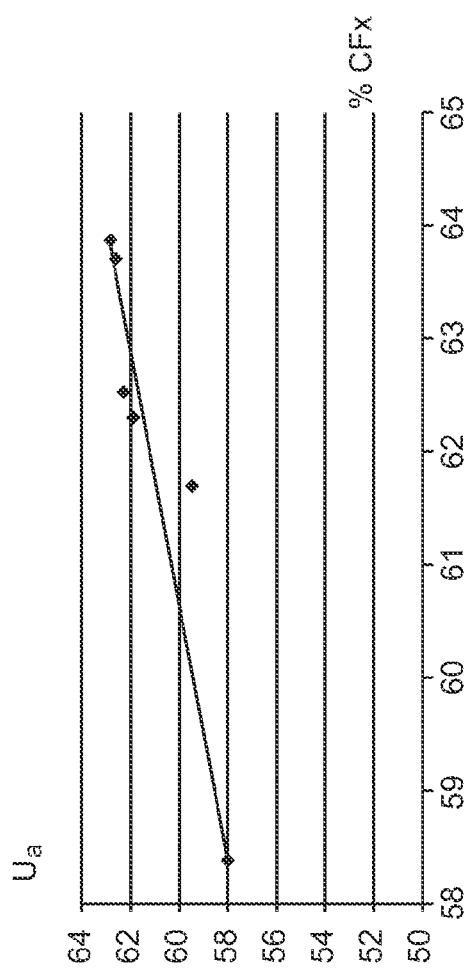
FIG. 14 presents the graph of dependence of subtractions of an apparatus on fluorine content in powder (measurements were executed for pallet No. 2). Correlation coefficient r=0.924.

Powder samples from squares nos. 8, 12, 20, 37, 44, 46 and 50 were subjected to chemical analysis. On FIG. 13 one can see 3-dimension graph of fluorine-concentration distribution in powder along co-ordinates in the pallet's plane. FIG. 14 shows a graph of dependence of subtractions of a calibrated apparatus on fluorine content in samples selected from pallet No. 2 at points 8, 12, 20, 37, 44, 46, 50. Table 11 shows values of errors in the process of determination of fluorine concentration at the given points of pallet No. 2

TABLE 11

Error values in the process of determination of fluorine concentration at the given points of pallet No. 2.

| | $C_F$, % | | | | | | |
|---|---|---|---|---|---|---|---|
| | 41.58 | 58.37 | 61.67 | 62.28 | 62.51 | 63.69 | 63.88 |
| $U_i$ | 52.0 | 58.1 | 59.5 | 61.9 | 62.3 | 62.6 | 62.6 |
| $\Delta_i = C_F - U_i$, % | −10.42 | 0.27 | 2.17 | 0.38 | 0.21 | 1.09 | 1.28 |

Errors obtained for all points are acceptable.

Apparatus's calibrating characteristics plotted using powder samples having various fluorine content turned out to be linear by measurement results followed by averaging out the results for each of the samples. That is, apparatus's subtractions are directly proportional to fluorine content in powders.

Correlation coefficients calculated for calibrating characteristics (regression lines) for powders in initial state and ones after mixing have insignificant difference: for powders in initial state r=0.967, for powders after mixing r=0.974. Equations of regression lines for powders in initial state and ones after mixing also have insignificant difference.

Measurement results at marked points of the pallet were compared with results of chemical analysis of powder samples collected at these points. Dependences of apparatus's subtractions on fluorine content in the selected samples for all three pallets have turned out to be linear ones with high correlation coefficient values. In the area of low and rather high fluorine concentration values, coincidence of measurement results with chemical analysis data is satisfactory. However, for small fluorine concentration values (11.39-28.01%), discrepancy between chemical analysis data and apparatus's subtractions is significant.

Figure 15:
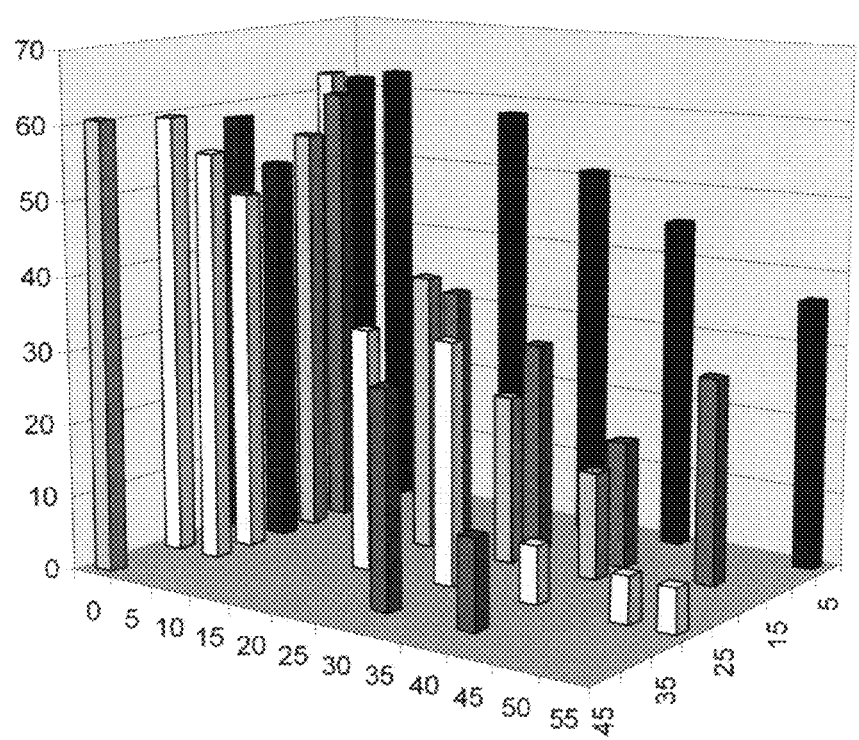
FIG. 15 shows the three-dimensional graph of fluorine-concentration distribution in CFx powder along co-ordinates in the plane of pallet No. 1. after fluorination process.
Figure 16:
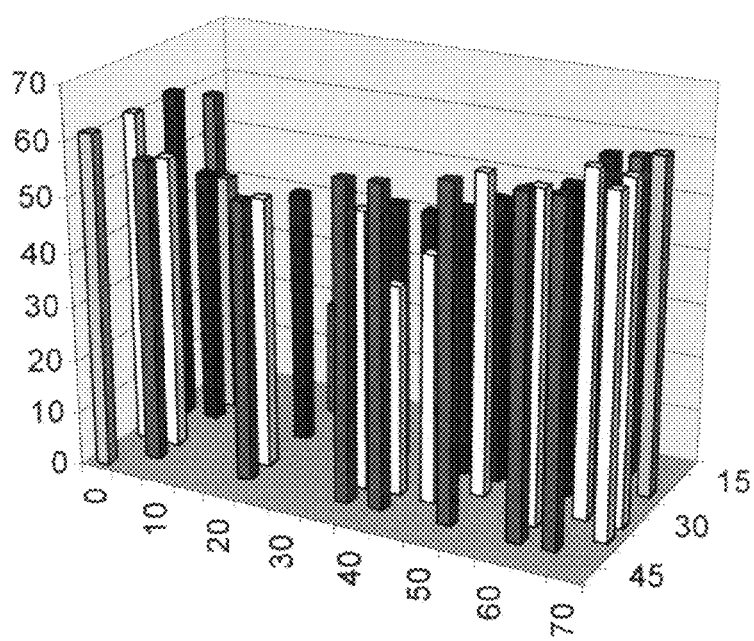
FIG. 16 shows the three-dimensional graph of fluorine-concentration distribution in CFx powder along co-ordinates in the plane of pallet No. 3. after fluorination process.

In FIGS. 15 and 16 show the results of measurements of the degree of oxidation with carbon fluoride on pallets #2 and 3. It demonstrates the uneven fluorination in the square pallets. Analysis of these figures shows that the proposed control method makes it possible to optimize these technological processes in determining the contour of thickness of carbon on the square pallets, sending streams of gaseous fluoride and temperature.

This is explained by the fact that both at low (4-5.37%) and rather high (over 40%) fluorine concentration, powder is more or less homogeneous. For the intermediate range of concentration, the powder is heterogeneous—fluorine concentration is much higher in near-surface layers than in deep layers. While measuring, the apparatus averages out powder concentration value within a control spot. Therefore, it is very difficult to select for chemical analysis a sample averaged out within a powder's control spot. This explains rather high error values within this concentration range.

The results of the non-destructive evaluation the level of the uniform distribution of the CFx degree of fluorination on the pallet can be used for optimization the parameters of the fluorination. Results of the rapid non-destructive analysis of the CFx compositions show that multiple measurements across the surface of a pallet, after measurement results were averaged out, will yield more accurate results than a single chemical analysis of a sample.

Measurements were conducted for powders having a different composition. In spite of the fact that the apparatus have not been calibrated on the basis of these powders, one has reached for most of those a good correspondence between apparatus's subtractions and chemical analysis data.

CLOSURE

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A system for non-destructive determination of a degree of fluorination in carbon powder, said system comprising:
    a measuring transducer coupled to a frequency generator, the measuring transducer configured to measure a respective capacitance of the carbon powder;
    a base transducer coupled to a frequency generator, the base transducer configured to measure a base capacitance; and
    a block for computing the difference between the respective capacitance and the base capacitance.

2. The system as in claim 1, wherein the measuring transducer includes a capacitance sensor.

3. The system as in claim 2, further comprising a scanner coupled with the capacitance sensor, the scanner configured to move the capacitance sensor horizontally along a flat plane and vertically into the carbon powder.

4. The system as in claim 3, wherein the scanner includes a counterweight to balance at least the weight of the capacitance sensor.

5. The system as in claim 1, wherein the frequency generator coupled to the measuring transducer is the frequency generator coupled to the base transducer.

6. The system as in claim 1, further comprising a block for determining the degree of fluorination in the carbon powder in accordance with the difference.

7. The system as in claim 1, wherein the measuring transducer is further configured to measure a respective Q factor thereof.

8. The system as in claim 1, wherein the capacitance sensor includes two electrodes each having a portion of a cylindrical surface.

9. The system as in claim 1, wherein the capacitance sensor includes coplanar round electrodes in the form of a disc surrounded by coaxial rings.

10. The system as in claim 9, wherein the capacitance sensor includes round electrodes in the form of a disc surrounded by four coaxial rings.

* * * * *